United States Patent [19]

Hubele

[11] 4,007,278
[45] Feb. 8, 1977

[54] 1-(1-CARBAMOYLOXY-2,2,2-TRICHLORO-ETHYL)-1,2,4-TRIAZOLE DERIVATIVES AS PESTICIDES

[75] Inventor: Adolf Hubele, Magden, Switzerland

[73] Assignee: Ciba-Geigy Corporation, Ardsley, N.Y.

[22] Filed: Feb. 7, 1975

[21] Appl. No.: 548,052

[30] Foreign Application Priority Data

Feb. 19, 1974 Switzerland ............... 2277/74
June 10, 1974 Switzerland ............... 7883/74
Dec. 20, 1974 Switzerland ............... 17033/74

[52] U.S. Cl. .................. 424/269; 71/92; 260/308 R
[51] Int. Cl.[2] .................. A01N 9/22; C07D 209/08
[58] Field of Search ............. 260/308 R; 424/269

[56] References Cited

FOREIGN PATENTS OR APPLICATIONS

| | | | |
|---|---|---|---|
| 1,186,467 | 2/1965 | Germany | 260/308 R |
| 1,543,604 | 10/1969 | Germany | 260/308 R |
| 1,901,421 | 8/1969 | Germany | 260/308 R |
| 1,795,249 | 12/1971 | Germany | 260/308 R |
| 2,201,063 | 7/1973 | Germany | 260/308 R |
| 1,319,479 | 6/1973 | United Kingdom | 260/308 B |

OTHER PUBLICATIONS

Carter et al, Ann. Appl. Biol., 1972, vol. 70, pp. 233–243.

Summers, Aust. J. Chem., vol. 25, pp. 671–675 (1972).
Zinner et al, Pharmazie, vol. 20, pp. 291–296 (1965).

*Primary Examiner*—Alton D. Rollins
*Attorney, Agent, or Firm*—Harry Falber

[57] ABSTRACT

Compounds of the formula I

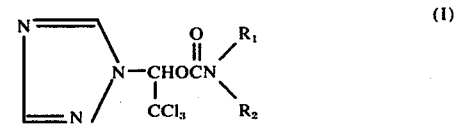

wherein $R_1$ represents hydrogen, $C_1$–$C_3$-alkyl or $C_1$–$C_3$-alkoxy, and $R_2$ represents $C_1$–$C_6$-alkyl or $C_3$–$C_4$-alkenyl both optionally substituted by cyano, halogen, nitro, $C_1$–$C_3$-alkoxy or $C_1$–$C_3$-alkylthio, or $C_3$–$C_8$-cycloalkyl or $C_3$–$C_8$-cycloalkenyl both optionally substituted by $C_1$–$C_3$-alkyl.

A particularly important group of compounds of formula I is that wherein $R_2$ represents a $C_1$–$C_4$-alkyl group, which are useful as pesticides especially as fungicides.

18 Claims, No Drawings

1-(1-CARBAMOYLOXY-2,2,2-TRICHLOROETHYL)-1,2,4-TRIAZOLE DERIVATIVES AS PESTICIDES

The present invention relates to 1-(1'-carbamoyloxy-2',2',2'-trichloroethyl)-1,2,4-triazole derivatives, to processes for producing them, as well as to compositions containing them and to their use for the control of pests.

The new 1,2,4-triazole derivatives correspond to formula I

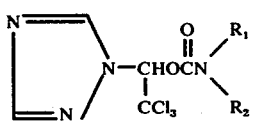

wherein
$R_1$ represents hydrogen, $C_1$–$C_3$-alkyl or $C_1$–$C_3$-alkoxy, and
$R_2$ represents $C_1$–$C_6$-alkyl or $C_3$–$C_4$-alkenyl both optionally substituted by cyano, halogen, nitro, $C_1$–$C_3$-alkoxy or $C_1$–$C_3$-alkylthio, or $C_3$–$C_8$-cycloalkyl or $C_3$–$C_8$-cycloalkenyl both optionally substituted by $C_1$–$C_3$-alkyl.

A particularly important group of compounds of formula I is that wherein $R_2$ represents a $C_1$–$C_4$-alkyl group.

Of interest are also compounds of formula I wherein $R_2$ represents cyclohexyl.

Within the aforementioned groups, preferred compounds are those wherein $R_1$ represents hydrogen.

By alkyl are meant, depending on the number of given carbon atoms, the following groups: methyl, ethyl, propyl, butyl, pentyl or hexyl, as well as isomers thereof such as, e.g., isopropyl, iso-, sec- or tert.-butyl, 1-methylbutyl, etc..

By alkenyl are meant the following groups: allyl and butenyl as well as isomers thereof.

Suitable as $C_3$–$C_8$-cycloalkyl or $C_3$–$C_8$-cycloalkenyl are e.g., the following groups: cyclopropyl, cyclopentyl, cyclohexyl, cyclohexenyl, cycloheptyl, cycloheptenyl, cyclooctyl, etc..

The halogens optionally present as substituents are fluorine, chlorine, bromine or iodine.

The alkoxy and alkylthio groups optionally present as substituents have as the alkyl moiety: methyl, ethyl, n-propyl or i-propyl.

The compounds of formula I can be produced according to the invention by a process in which a compound of formula II

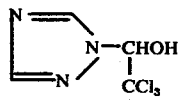

is reacted
a. with a compound of formula III

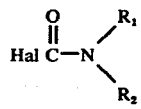

in the presence of an acid-binding agent, or
b. in the case where $R_1$ represents hydrogen, with a compound of the formula $$OCNR_2 \qquad (IV),$$

whereby in formulae III and IV, $R_1$ and $R_2$ have the meanings given under formula I, and Hal stands for halogen, preferably for chlorine or bromine.

The compound of formula II is produced in a manner known per se, such as, e.g., by the reaction of 1,2,4-triazole with chloral. This compound is new and exhibits a certain bactericidal action.

The reactions can be performed in anhydrous solvents or diluents which are inert to the reactants, such as aliphatic, aromatic and/or halogenated hydrocarbons such as, e.g., benzene, toluene or chloroform; in ethers such as, e.g., diethyl ether, dioxane or tetrahydrofuran; in ketones such as, e.g., acetone or methyl ethyl ketone; in nitriles such as, e.g., acetonitrile; in esters such as, e.g., acetic acid esters, as well as in mixtures of such solvents.

The reactions according to (b) are performed advantageously in the presence of catalytic amounts of tertiary amines such as, e.g., triethylamine, triethylenediamine, etc..

In the reactions according to (a), it is possible to use as acid-binding agent preferably equimolar amounts of tertiary amines such as, e.g., triethylamine.

The reactions are carried out at temperatures of between $-20°$ and $+120°$ C, preferably between $+10°$ and $+40°$ C, and at normal pressure.

A number of the compounds of formula I are suitable for the control of phytopathogenic bacteria on corn, maize, potatoes, rice, vegetables, grape vines, ornamental plants and fruit and on other cultivated crops.

As phytopathogenic bacteria, there may be mentioned, inter alia, members of the order Pseudomonas, for example *Pseudomonas tomato*, *Pseudomonas lachrymans* and *Pseudomonas phaseolicola*, Xanthomonas, e.g. *Xanthomonas oryzae*, *Xanthomonas vesicatoria* and *Xanthomonas phaseoli*, as well as Erwinia and Corynebacterium.

Some compounds of formula I have in certain cultivated crops of useful plants a selective herbicidal action against weeds.

To be emphasised is, however, the action of compounds of formula I against phytopathogenic fungi. They are effective, for example, against Phycomycetes such as *Phytophthora infestans*, Ascomycetes such as *Erysiphe graminis*, and against Fungi imperfecti such as *Piricularia oryzae*, *Fusarium oxysporum* and *Verticillium albo-atrum*.

A particular property of compounds of formula I is their systemic action, i.e. their ability to be conveyed in a plant to a site of infection that is remote from the point of application. Thus, such a compound can, after treatment of the soil, be taken up by the roots of a plant and then transported to the site of infection.

The compounds of formula I can be applied to all parts of plants. For the widening of their range of action, the compounds of formula I may of course be used together with other suitable pesticidal active substances or active substances promoting plant growth.

The compounds of formula I can be used on their own or together with suitable carriers and/or additives. Suitable carriers and additives may be solid or liquid, and correspond to the substances common in formulation practice, such as natural and regenerated mineral substances, solvents, dispersing agents, wetting agents, adhesives, thickeners, binders and fertilisers. Such compositions are produced in a manner known per se by the intimate mixing and grinding of the constituents.

For application, the compounds of formula I can be in the following forms:

solid preparations: dusts, scattering agents, granulates, coated granulates, impregnated granulates and homogeneous granulates;

liquid preparations:
a. water-dispersible active-substance concentrates: wettable powders, pastes or emulsions;
b. solutions.

The content of active substance in the above described preparations is between 0.1 and 95 per cent by weight. The active substances of formula I can be formulated, for example, as follows.

Dusts:
The following substances are used in the preparation of (a) a 5% dust, and (b) a 2% dust:
a. 5 parts of active substance,
95 parts of talcum;
b. 2 parts of active substance,
1 part of highly dispersed silicic acid,
97 parts of talcum.

The active substances are mixed and ground with the carriers.

Granulate:
The following substances are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The resulting solution is sprayed on to kaolin, and the acetone is subsequently evaporated off in vacuo.

Wettable powder:
The following constituents are used in the preparation of (a) a 40%, (b) and (c) a 25%, and (d) a 10% wettable powder:
a. 40 parts of active substance,
5 parts of sodium lignin sulphonate,
1 part of sodium dibutyl-naphthalene sulphonate,
54 parts of silicic acid;
b. 25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;
d. 10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates:
The following substances are used to produce a 25% emulsifiable concentrate:
a. 25 parts of active substance,
2.5 parts of epoxidised vegetable oil,
10 parts of alkylarylsulphonate/fatty alcohol polyglycol ether mixture,
5 parts of dimethylformamide,
57.5 parts of xylene.

From such concentrates it is possible to prepare, by dilution with water, emulsions of any desired concentration.

The following examples serve to further illustrate the invention without limiting the scope thereof. The temperature values are given in degrees Centigrade.

EXAMPLE 1

Preparation of 1-(1'-n-propylcarbamoyloxy-2',2',2'-trichloroethyl)-1,2,4-triazole of the formula

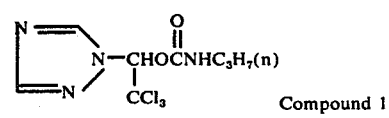

Compound 1 a. Preparation of 1-(1'-hydroxy-2',2',2'-trichloroethyl)-1,2,4-triazole of formula II

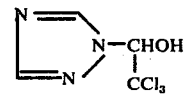

118 g of chloral in 50 ml of acetone was added at room temperature, with thorough stirring, to 50 g of 1,2,4-triazole in 500 ml of acetone. After the slightly exothermic reaction had subsided, the resulting precipitate was filtered off and subsequently washed with acetone. The white crystals melt at 143.5° – 145° C with decomposition.

b. To a suspension of 22 g of 1-(1'-hydroxy-2',2',2'-trichloroethyl)-1,2,4-triazole in 250 ml of ethyl acetate there was added 1 ml of triethylamine. There was then added dropwise at room temperature within one hour, with good stirring, 9.6 g of n-propylisocyanate in 50 ml of ethyl acetate. The mixture was further stirred for 24 hours; the resulting clear solution was concentrated by evaporation to dryness and recrystallised from toluene/petroleum ether. Melting point of Compound 1 = 88°–90°.

EXAMPLE 2

Production of 1-[1'-(N-methoxy-N-methylcarbamoyloxy)-2',2',2'-trichloroethyl]-1,2,4-triazole of the formula

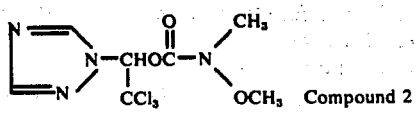
Compound 2

To a suspension of 21.7 g of 1-(1'-hydroxy-2',2',2'-trichloroethyl)-1,2,4-triazole in 40 ml of chloroform there were simultaneously added dropwise at room temperature within one hour, with good stirring, 13.6 g of methoxymethylcarbamoyl chloride in 20 ml of benzene and 11 g of triethylamine in 20 ml of benzene. After twelve hours' stirring, the reaction mixture was washed twice with water for removal of the triethylamine hydrochloride; it was then dried over sodium sulphate, and the solution was concentrated by evaporation to dryness and caused to crystallise with petroleum ether. After recrystallisation from diethyl ether, the white crystals of Compound 2 melt between 78° and 80°.

The following 1-(1'-carbamoyloxy-2',2',2'-trichloroethyl)-1,2,4-triazoles were produced in an analogous manner: X-carbamoyloxy-2',2',2'-trichloroethyl)-1,2,4-triazole

| Compound No. | X | Physical data (0° C) |
|---|---|---|
| 3 | 1-(1'-methyl | M.P. 163–165° |
| 4 | 1-(1'-ethyl | M.P. 107–109° |
| 5 | 1-(1'-β-chloroethyl | M.P. 115–118° |
| 6 | 1-(1'-β-methoxyethyl | M.P. 102–107° |
| 7 | 1-(1'-iso-propyl | M.P. 102–104° |
| 8 | 1-(1'- n-butyl | M.P. 79–81° |
| 9 | 1-(1'-t-butyl | M.P. 126–128° |
| 10 | 1-(1'-allyl | M.P. 78–80° |
| 11 | 1-(1'-cyclohexyl | M.P. 112–113° |
| 12 | 1-(1'-N,N-dimethyl | M.P. 118–119° |
| 13 | 1-(1'-α-cyano-iso-propyl | |
| 14 | 1-(1'-n-hexyl | |
| 15 | 1-(1'-(2-butenyl) | |
| 16 | 1-(1'-cyclopropyl | |
| 17 | 1-(1'-cyclohexyl | |
| 18 | 1-(1'-cycloheptyl | |
| 19 | 1-(1'-β-methylthioethyl | |
| 20 | 1-(1'-cyclohexenyl | |
| 21 | 1-(1'-(3-methylcyclohexyl) | |

EXAMPLE 3

Action against *Erysiphe graminis* on *Hordeum vulgare* a. Residual protective action

Barley plants about 8 cm in height were sprayed with a spray mixture prepared from wettable powder of the active substance (0.05% active substance). After 48 hours the treated plants were dusted with conidia of the fungus. The infected barley plants were placed in a greenhouse at about 22° C and the fungus infestation was assessed after 10 days.

The compounds Nos. 1, 2, 3, 4, 7, 8, 9 and 11 exhibited a good action (i.e. plants less than 20% infested, compared with untreated but infected control plants).

b. Systemic action

Barley plants about 8 cm in height were watered with a spray mixture produced from wettable powder of the active substance (0.01% active substance relative to the volume of soil). Care was taken to ensure that the spray mixture did not come into contact with the parts of the plants above the soil. After 48 hours, the treated plants were dusted with conidia of the fungus. The infected barley plants were placed in a greenhouse at approx. 22° C and the fungus infestation was assessed after 10 days.

The Compounds Nos. 1, 3, 4, 7, 8 and 9 exhibited a good action (i.e. plants less than 20% infested compared with untreated but infected control plants).

EXAMPLE 4

Action against *Piricularia oryzae* on *Oryzae sativa*

Residual protective action

Rice plants were sprayed after two weeks' cultivation with a spray mixture prepared from wettable powder of the active substance (0.02% active substance). After 48 hours, the treated plants were infected with a conidia suspension of the fungus. After 5 days' incubation at 95–100% relative humidity and 24° C, the fungus infestation was assessed.

Compound No. 8 exhibited a good action (i.e. plants less than 20% infested, compared with untreated but infected control plants).

EXAMPLE 5

Action against *Xanthomonas vesicatoria* on paprika

Young paprika plants were sprayed dripping wet with the active substance in the form of a spray mixture having 1000 ppm active-substance content.

One day after application, the plants were infected with a suspension of the bacteria by the spraying of the underside of the primary leaves, and subsequently incubated for 8 days at 22° C and 95% relative humidity. After this period of time, an evaluation is made on the basis of the number of typical disease spots.

The compounds Nos. 3, 4, 5, 8 and 7 exhibited a good action (i.e. plants less than 20% infested, compared with untreated but infected control plants.

I claim:

1. A compound of formula I

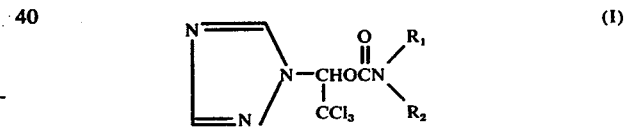

wherein
R$_1$ represents hydrogen, C$_1$–C$_3$-alkyl or C$_1$–C$_3$-alkoxy, and
R$_2$ represents C$_1$–C$_6$-alkyl or C$_3$–C$_4$-alkenyl both optionally substituted by cyano, halogen, nitro, C$_1$–C$_3$-alkoxy or C$_1$–C$_3$-alkylthio, or C$_3$–C$_8$-cycloalkyl or C$_3$–C$_8$-cycloalkenyl both optionally substituted by C$_1$–C$_3$-alkyl.

2. The compound according to claim 1, wherein R$_2$ represents C$_1$–C$_4$-alkyl.

3. The compound according to claim 1, wherein R$_2$ represents cyclohexyl.

4. The compound according to claim 1, wherein R$_1$ represents hydrogen.

5. 1-(1'-n-Propylcarbamoyloxy-2',2',2'-trichloroethyl)-1,2,4-triazole.

6. 1-(1'-Methylcarbamoyloxy-2',2',2'-trichloroethyl)-1,2,4-triazole.

7. 1-(1'-Ethylcarbamoyloxy-2',2',2'-trichloroethyl)-1,2,4-triazole.

8. 1-(1'-n-Butylcarbamoyloxy-2',2',2'-trichloroethyl)-1,2,4-triazole.

9. 1-(1'-iso-Propylcarbamoyloxy-2',2',2'-trichloroethyl)-1,2,4-triazole.

10. 1-(1'-t-Butylcarbamoyloxy-2',2',2'-trichloroethyl)-1,2,4-triazole.

11. 1-(1'-Cyclohexylcarbamoyloxy-2',2',2'-trichloroethyl)-1,2,4-triazole.

12. A microbicidal composition comprising as active component a microbicidally effective amount of a compound according to claim 1, together with a suitable inert carrier therefor.

13. The composition of claim 12, wherein said compound is 1-(1'-n-Butylcarbamoyloxy-2',2',2'-trichloroethyl)-1,2,4-triazole.

14. The composition of claim 12, wherein said compound is 1-(1'-t-Butylcarbamoyloxy-2',2',2'-trichloroethyl)-1,2,4-triazole.

15. A method for combatting microbes which comprises applying to the locus thereof a microbicidally effective amount of a compound according to claim 1.

16. The method of claim 15 for combatting phytopathogenic fungi.

17. The method of claim 16, wherein said compound is 1-(1'-n-Butylcarbamoyloxy-2',2',2'-trichloroethyl)-1,2,4,-triazole.

18. The method of claim 16, wherein said compound is 1-(1'-t-Butylcarbamoyloxy-2',2',2'-trichloroethyl)-1,2,4-triazole.

* * * * *